United States Patent [19]

O'Lenick, Jr.

[11] Patent Number: 5,639,897
[45] Date of Patent: Jun. 17, 1997

[54] AMIDO ETHER AMINE AMPHOTERIC SURFACTANTS

[76] Inventor: Anthony J. O'Lenick, Jr., 743 Ridgeview Dr., Lilburn, Ga. 30247

[21] Appl. No.: 568,566

[22] Filed: Dec. 7, 1995

[51] Int. Cl.$^6$ ............................................. C07C 231/00
[52] U.S. Cl. ............................................. 554/59; 562/564
[58] Field of Search ............................... 562/564; 554/59

[56] References Cited

U.S. PATENT DOCUMENTS

| | | | |
|---|---|---|---|
| 2,195,974 | 5/1940 | Reppe . | |
| 2,781,375 | 2/1957 | Mannheimer | 562/564 |
| 2,781,379 | 2/1957 | Mannheimer | 562/564 |
| 2,781,389 | 2/1957 | Mannheimer | 562/564 |
| 2,891,873 | 6/1959 | Falkenberg | 554/59 |
| 2,961,451 | 11/1960 | Keough | 554/59 |
| 2,970,160 | 1/1961 | Walker | 554/59 |
| 2,993,918 | 7/1961 | Mannheimer | 562/564 |
| 3,129,106 | 4/1964 | Katz | 554/59 |
| 3,417,136 | 12/1968 | Hovden . | |
| 5,196,589 | 3/1993 | O'Lenick . | |

*Primary Examiner*—Michael L. Shippen

[57] ABSTRACT

The present invention deals with novel novel amido amines amphoteric surfactants which contain ether functionalities. The utility for these novel polymers is as softening, antitangle, and conditioning agents for use in personal care, textile and related applications. The properties of these novel amphoteric polymeric compositions which makes them well suited for these applications is the fact that they are substantive to fibers, hair and skin and also very mild to the skin and eyes.

17 Claims, No Drawings

AMIDO ETHER AMINE AMPHOTERIC SURFACTANTS

FIELD OF THE INVENTION

The present invention deals with novel compounds, their application, intermediates useful in their preparation and a process for the preparation. The compounds are novel amido amines amphoteric compounds which contain ether functionalities. The intermediate is a novel ether containing amido amine. The utility for these novel polymers is as softening, anti-tangle, and conditioning agents for use in personal care, textile and related applications. The properties of these novel amphoteric polymeric compositions which makes them well suited for these applications is the fact that they are substantive to fibers, hair and skin and also very mild to the skin and eyes.

DESCRIPTION OF THE ART PRACTICES

Aminocarboxylic amphoteric surfactants have been known and used commercially for many years. Perhaps the most important early patent on the production of these materials is U.S. Pat. No. 2,195,974 to Reppe et al. The patent, issued in May 1936 and assigned to I. G. Farben, discloses the reaction of acrylic acid, methacrylic acid and ammonia or organic amines at temperatures at which amides do not form. The patent described many reaction conditions in addition many solvents were described ranging from water to other protic solvents. Reppe also describes many so called "acrylic sources", which are suitable as raw materials for preparation of this class of amphoteric surfactants.

The surfactant properties of aminocarboxylic acids and salts are likewise well known to those skilled in the art. Over the years, these compounds have been found to have limited usefulness as foaming agents and detergents in some applications. The compounds have not enjoyed wider use in other applications, due to the fact the prior art compounds lack compatibility with anionic surface active agents, are not mild when applied to the eye and skin U.S. Pat. No. 3,417,136 issued to Hovden Dec. 17, 1968, attempts to develop a product with increased water solubility by incorporating an ether function into the molecule. Hovden states prior to his invention, the known aminocarboxylic acid surfactant compounds have a lesser water solubility than is desired in some applications. Further, he states many of these compounds do not have as great a wetting power as might be desired for certain applications. This is also a function of water solubility. While Hovden's invention solved the difficulty of obtaining a series of products which are more water soluble and have improved wetting properties, it remained a problem to produce products with the desired anionic compatibility and mildness and electrolyte compatibility.

OBJECTS OF THE INVENTION

It is the object of this invention to produce amido containing amphoteric polymer compositions that have improved are highly substantive to hair, skin and fibers, have low irritation properties when placed on the skin or in the eyes, and are compatible with anionic surfactants. This improved performance relates to the fact that the products of this invention (a) contain fatty amido groups which result unexpected mildness and compatibility with anionic surfactants and (b) contain an ether functionality which results amphoterics with unique solubility, and emulsification properties in a variety of solvents. These materials also provide stable copious foam and much improved detergency properties over traditional amino proprionates.

Another object of the invention is to provide a novel class of amido ether amphoteric compounds which exhibit outstanding surface active properties. They have high foam properties and are much less sensitive to calcium ions than standard proprionates.

Still another object of the invention is a process for the treatment of skin, hair and fibers with an effective conditioning amount of the compounds of the invention.

Other objects of the invention will become clear from the disclosure.

THE INVENTION

The first set of compounds of the present invention are the amido ether amines which are the raw materials upon which the present invention is based. These materials are prepared by cyanoethylation of alkanolamides with acrylonitrile followed by hydrogenation to make an amido ether amine. These intermediate compounds conform to the following structure;

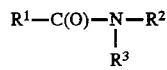

$R^1$ is alkyl having from 5 to 19 carbon atoms;

$R^2$ is $-(R^4)n-O-(CH_2)_3-NH_2$;

$R^3$ is selected from the group consisting of H and $-(CH_2)n-O-(CH_2)_3-NH_2$;

$R^4$ is lower alkyl selected from the group consisting of $-CH_2-$ and $-CH(CH_3)-$;

n is an integer from 1 to 3.

The reaction of the hydroxyl group in the alkanolamide with acrylonitrile followed by hydrogenation produces an ether containing amido amine which is a key heretofore unknown material. The overall reaction is shown below;

Monosubstituted Product
($R^3$ is H)

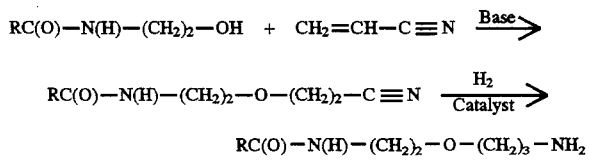

(Ether Amido Amine Intermediate Class 1)

Disubstituted product $R^3$ is not H;

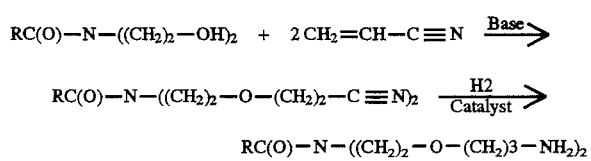

(Di-ether Amido Amine Intermediate Class 2)

Another aspect of this invention is an amphoteric based upon the reaction of the above ether containing ether containing amido amine with an unsaturated carboxylic acid or ester selected from the group consisting of acrylic acid, methyl acrylate, crotic acid and methacrylic acid to produce a high purity amphoteric compound which has unique unexpected surface active properties.

Amphoteric compounds of the present invention conform to the following structure;

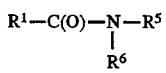

$R^1$ is alkyl having from 5 to 19 carbon atoms;

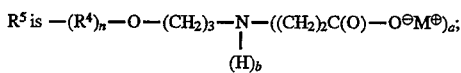

a is 1 or 2 and b is 0 or 1, with the proviso that a+b is equal to 2;

$R^6$ is selected from the group consisting of H and

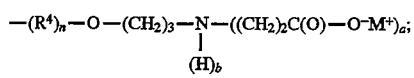

M is hydrogen or any positively charged salt forming radical;

$R^4$ is lower alkyl selected from the group consisting of $-CH_2-$ and $-CH(CH_3)-$;

n is an integer from 1 to 3.

It will be clearly understood that the amphoteric compounds of the present invention will have the following additional functional groups per amino group reacted; (a) one or two carboxyl groups (depending upon stiochiometric amounts of acid reacted), (b) one amido group and (c) one ether group.

In the case were R3 is not H a branched product results which has two primary amine groups present, between 2 and 4 carboxyl groups and two ether groups.

PREFERRED EMBODIMENTS

In a preferred embodiment $R^3$ is H.
In another preferred embodiment $R^3$ is:

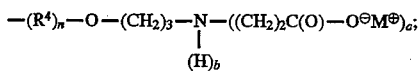

In a preferred embodiment $R^4$ is $-CH_2-$.
In a preferred embodiment $R^4$ is $-CH(CH_3)-$;
In a preferred embodiment $R^1$ is alkyl having 5 carbon atoms.
In a preferred embodiment $R^1$ is alkyl having 7 carbon atoms.
In a preferred embodiment $R^1$ is alkyl having 9 carbon atoms.
In a preferred embodiment $R^1$ is alkyl having 11 carbon atoms.
In a preferred embodiment $R^1$ is alkyl having 13 carbon atoms.
In a preferred embodiment $R^1$ is alkyl having 15 carbon atoms.
In a preferred embodiment $R^1$ is alkyl having 17 carbon atoms.
In a preferred embodiment $R^1$ is alkyl having 19 carbon atoms.

The novel amphoteric surfactant compounds of the present invention include both acids and salts thereof, and in the above formula "M" may be hydrogen or any positively charged salt forming radical, e.g., alkali metal, ammonium or ethanolamine.

EXAMPLES

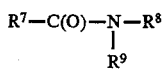

$R^7$ is alkyl having from 5 to 19 carbon atoms;
$R^8$ is $-(R^{10})_n-OH$
$R^9$ is selected from the group consisting of H and $-(CH_2)_nOH$
$R^{10}$ is lower alkyl selected from the group consisting of $-CH_2-$ and $-CH(CH_3)-$;
n is an integer from 1 to 3.

Monoethanolamide Products (Examples 1–8)

The first series of alkanolamides are items of commerce made by the reaction of monoethanolamine with a fatty acid or preferably a fatty ester. The process is well known to those skilled in the art.

| Example | $R^7$ | $R^9$ | $R^{10}$ | n |
|---|---|---|---|---|
| 1 | $C_5H_{11}$ | H | $CH_2$ | 2 |
| 2 | $C_7H_{13}$ | H | $CH_2$ | 2 |
| 3 | $C_9H_{17}$ | H | $CH_2$ | 2 |
| 4 | $C_{11}H_{21}$ | H | $CH_2$ | 2 |
| 5 | $C_{13}H_{25}$ | H | $CH_2$ | 2 |
| 6 | $C_{15}H_{29}$ | H | $CH_2$ | 2 |
| 7 | $C_{17}H_{33}$ | H | $CH_2$ | 2 |
| 8 | $C_{19}H_{37}$ | H | $CH_2$ | 2 |

Diethanolamide Products (Examples 9–16)

The second series of alkanolamides are items of commerce made by the reaction of diethanolamine with a fatty acid or preferably a fatty ester. The process is well known to those skilled in the art.

| Example | $R^7$ | $R^9$ | $R^{10}$ | n |
|---|---|---|---|---|
| 9 | $C_5H_{11}$ | $(CH_2)_n-OH$ | $CH_2$ | 2 |
| 10 | $C_7H_{13}$ | $(CH_2)_n-OH$ | $CH_2$ | 2 |
| 11 | $C_9H_{17}$ | $(CH_2)_n-OH$ | $CH_2$ | 2 |
| 12 | $C_{11}H_{21}$ | $(CH_2)_n-OH$ | $CH_2$ | 2 |
| 13 | $C_{13}H_{25}$ | $(CH_2)_n-OH$ | $CH_2$ | 2 |
| 14 | $C_{15}H_{29}$ | $(CH_2)_n-OH$ | $CH_2$ | 2 |
| 15 | $C_{17}H_{33}$ | $(CH_2)_n-OH$ | $CH_2$ | 2 |
| 16 | $C_{19}H_{37}$ | $(CH_2)_n-OH$ | $CH_2$ | 2 |

Diethanolamide Products (Examples 17–24)

The third series of alkanolamides are items of commerce made by the reaction of monoisopropanolamine with a fatty acid or preferably a fatty ester. The process is well known to those skilled in the art.

| Example | $R^7$ | $R^9$ | $R^{10}$ | n |
|---|---|---|---|---|
| 17 | $C_5H_{11}$ | H | $CH_2CH(CH_3)$ | 1 |
| 18 | $C_7H_{13}$ | H | $CH_2CH(CH_3)$ | 1 |
| 19 | $C_9H_{17}$ | H | $CH_2CH(CH_3)$ | 1 |
| 20 | $C_{11}H_{21}$ | H | $CH_2CH(CH_3)$ | 1 |
| 21 | $C_{13}H_{25}$ | H | $CH_2CH(CH_3)$ | 1 |
| 22 | $C_{15}H_{29}$ | H | $CH_2CH(CH_3)$ | 1 |
| 23 | $C_{17}H_{33}$ | H | $CH_2CH(CH_3)$ | 1 |
| 24 | $C_{19}H_{37}$ | H | $CH_2CH(CH_3)$ | 1 |

Monoisopropanolamide Products (Examples 25–32)

The final series of alkanolamides are items of commerce made by the reaction of monoisopropanolamine with a fatty acid or preferably a fatty ester. The process is well known to those skilled in the art.

| Example | R7 | R9 | R10 | n |
| --- | --- | --- | --- | --- |
| 25 | $C_5H_{11}$ | $CH_2CH(CH_3)$ | $CH_2CH(CH_3)$ | 1 |
| 26 | $C_7H_{13}$ | $CH_2CH(CH_3)$ | $CH_2CH(CH_3)$ | 1 |
| 27 | $C_9H_{17}$ | $CH_2CH(CH_3)$ | $CH_2CH(CH_3)$ | 1 |
| 28 | $C_{11}H_{21}$ | $CH_2CH(CH_3)$ | $CH_2CH(CH_3)$ | 1 |
| 29 | $C_{13}H_{25}$ | $CH_2CH(CH_3)$ | $CH_2CH(CH_3)$ | 1 |
| 30 | $C_{15}H_{29}$ | $CH_2CH(CH_3)$ | $CH_2CH(CH_3)$ | 1 |
| 31 | $C_{17}H_{33}$ | $CH_2CH(CH_3)$ | $CH_2CH(CH_3)$ | 1 |
| 32 | $C_{19}H_{37}$ | $CH_2CH(CH_3)$ | $CH_2CH(CH_3)$ | 1 |

Preparation of Amido Ether Amine Intermediate

General Procedure

The amido ether amines are prepared by reacting alkanolamides with acrylonitrile in the presence of an alkaline catalyst, e.g., benzyl trimethyl ammonium hydroxide, potassium hydroxide, sodium methoxide, or sodium hydroxide, to form B-alkoxypropionitrile. The alkanolamide is reacted with the acrylonitrile at temperatures between about 25 C., and about 80 C., in the presence of about 0.1 percent potassium hydroxide for a period of about five to about six hours. The reaction is generally exothermic.

The B-alkoxypropionitrile is then hydrogenated in the presence of a suitable catalyst, e.g., Raney nickel, to form an alkoxypropylamine. The hydrogenation of the oxypropionitrile is preferably carried out at a temperature of 125 C., with a hydrogen partial pressure of about 300 psig.

U.S. Pat. No. 5,196,589 to O'Lenick, issued in 1993, which is incorporated herein by reference, teaches that certain free radical polymer inhibitors can be used to produce higher yields of the desired products, while minimizing the undesirable by products. Since the reaction is carried out on liquid amides, the inhibitors mentioned in the above referenced patent, are added to those amides which have a melting point above 50C.

EXAMPLES 33–64

The specified amount of the specified alkanolamide is reacted with the specified amount of acrylonitrile. The hydrogenation is carried out as specified.

| | Amide Reactant | | Acrylonitrile |
| --- | --- | --- | --- |
| Example | Example | Grams | Grams |
| 33 | 1 | 128.0 | 53.0 |
| 34 | 2 | 154.0 | 53.0 |
| 35 | 3 | 182.0 | 53.0 |
| 36 | 4 | 210.0 | 53.0 |
| 37 | 5 | 238.0 | 53.0 |
| 38 | 6 | 266.0 | 53.0 |
| 39 | 7 | 294.0 | 53.0 |
| 40 | 8 | 322.0 | 53.0 |
| 41 | 9 | 198.0 | 110.0 |
| 42 | 10 | 215.0 | 110.0 |
| 43 | 11 | 243.0 | 110.0 |
| 44 | 12 | 271.0 | 110.0 |
| 45 | 13 | 299.0 | 110.0 |
| 46 | 14 | 327.0 | 110.0 |
| 47 | 15 | 355.0 | 110.0 |
| 48 | 16 | 383.0 | 110.0 |
| 49 | 17 | 141.0 | 110.0 |
| 50 | 18 | 167.0 | 110.0 |
| 51 | 19 | 195.0 | 110.0 |
| 52 | 20 | 223.0 | 110.0 |
| 53 | 21 | 257.0 | 110.0 |
| 54 | 22 | 279.0 | 110.0 |
| 55 | 23 | 307.0 | 110.0 |
| 56 | 24 | 335.0 | 110.0 |
| 57 | 25 | 224.0 | 55.0 |
| 58 | 26 | 241.0 | 55.0 |
| 59 | 27 | 269.0 | 55.0 |
| 60 | 28 | 297.0 | 55.0 |
| 61 | 29 | 325.0 | 55.0 |
| 62 | 30 | 353.0 | 55.0 |
| 63 | 31 | 381.0 | 55.0 |

Amphoteric Preparation

GENERAL PROCEDURE

In a suitable three neck flask equipped with agitation and thermometer, is added 1000 grams of water, 72.0 grams of acrylic acid and 500 ppm hydroquinone mono methylether. Next, the specified amount of the specified amido ether amine reactant (examples 33–63) is added. The reaction mass will thicken as heat is applied. At about 80°–90 C. the viscosity thins out. Hold at this temperature 5 to 9 hours. The reaction is complete when the tertiary amine concentration reaches at least 97% of theoretical.

Add enough base to neutralize the product to a pH of 7 to 8. Addition is exothermic and is controlled by submersion of the flask into a cooling bath.

The product is now present in aqueous solution and can be used without purification or can be dried down in a rotoevaporator if desired.

| | Amide Reactant | | Acrylic Acid |
| --- | --- | --- | --- |
| Example | Example | Grams | Grams |
| 64 | 34 | 181.0 | 75.0 |
| 65 | 35 | 207.0 | 75.0 |
| 66 | 36 | 235.0 | 75.0 |
| 67 | 37 | 263.0 | 75.0 |
| 68 | 38 | 291.0 | 75.0 |
| 69 | 39 | 319.0 | 75.0 |
| 70 | 40 | 347.0 | 75.0 |
| 71 | 41 | 304.0 | 75.0 |
| 72 | 42 | 321.0 | 150.0 |
| 73 | 43 | 349.0 | 150.0 |
| 74 | 44 | 377.0 | 150.0 |
| 75 | 45 | 327.0 | 150.0 |
| 76 | 46 | 405.0 | 150.0 |
| 77 | 47 | 433.0 | 150.0 |
| 78 | 48 | 461.0 | 150.0 |
| 79 | 49 | 489.0 | 150.0 |
| 80 | 50 | 247.0 | 150.0 |
| 81 | 51 | 270.0 | 150.0 |
| 82 | 52 | 301.0 | 150.0 |
| 83 | 53 | 337.0 | 150.0 |
| 84 | 54 | 363.0 | 150.0 |
| 85 | 55 | 385.0 | 150.0 |
| 86 | 56 | 413.0 | 150.0 |
| 87 | 57 | 441.0 | 150.0 |
| 88 | 58 | 330.0 | 75.0 |
| 89 | 59 | 347.0 | 75.0 |
| 90 | 60 | 375.0 | 75.0 |
| 91 | 61 | 403.0 | 75.0 |
| 92 | 62 | 431.0 | 75.0 |
| 93 | 63 | 459.0 | 75.0 |
| 94 | 64 | 487.0 | 75.0 |

APPLICATIONS EXAMPLES

The amphoteric compounds of this invention can be formulated into softeners that are applied directly in aqueous solution by themselves or formulated with anionic, nonionic or amphoteric surfactants and builders to prepare finished conditioner/detergent systems. The level of composition of the present invention is typically used at a weight ratio to water of about 1:10:000 to 1:20 to soften fabric. Conditioners and Shampoos using the compositions employ it at 2% to 30% by weight. Anionic surfactants include lauryl and stearyl sulfate as well as alkylbenzene sulfonates, preferably the sodium salts. Nonionic surfactants include alkylalkoxylates typically having from 10 to 20 carbon atoms in the alkyl group and from 1 to 10 alkylene oxide units (preferably ethylene). Builders include the phosphates STPP and SPP as well as aluminosilicates.

Color Fastness Application Data

The amphoteric compounds of this invention were compared to standard compounds commercially available using AATCC Test Method 117–1979. The color fastness heat test uses a 400 F. (205 F.) hot iron which is applied for 60 and 180 seconds. The color is rated on a 1–5 basis for yellowness, (5 being the most yellow).

| Compound | CAS Number | Yellowness |
|---|---|---|
| Alkaquat O | 68122-86-1 | 4 |
| Stearyldimethyl Benzylalkonium Chloride | 61789-81-9 | 4 |
| Alkaquat DAET-90 | 65098-88-6 | 5 |
| Stearylamidopropyl amine Hydrochloride salt | 68308-45-2 | 4 |
| Examlpe #65 | | 2 |
| Example #85 | | 2 |
| Example #67 | | 2 |
| Example #77 | | 2 |

Wet Comb Out Test

A laboratory test is conducted to screen the wet comb properties of a representative member of the family of novel compositions. Hair swatches are purchased from a supply of human hair from the same head. Each test swatch contains 7 grams of hair and is 11 inches in length. The hair is tied tightly 1 inch from one end with string. The swatch is pre-cleaned with a 3% solution of ammonium lauryl sulfate. Subsequently, the swatch is washed under running tap water. The hair is then squeezed out and while still damp dipped into a 200 ml solution of 0.2% active product. Another rinse is made, then the swatch is blotted dry. The swatch is then treated by holding the hair swatch, combing the hair as rapidly as possible while alternating the side of the swatch combed. The time needed to get one smooth free stroke without tangling is recorded. Typical results for the standard quaternary compounds used in hair conditioning (stearyldimethylbenzyl ammonium chloride) range from 12–14 seconds.

| Rinse Conditioner (Net Comb Out Test) | |
|---|---|
| Product | Time in Seconds |
| Example #65 | 11 |
| Example #68 | 13 |
| Stearyldimethylbenzyl ammonium chloride | 12 |

What is claimed:

1. An amphoteric compound conforming to the following structure;

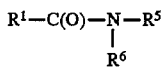

$R^1$ is alkyl having from 5 to 19 carbon atoms;

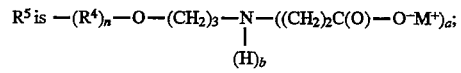

a is 1 or 2 and b is 0 or 1, with the proviso that a+b is equal to 2;

$R^6$ is selected from the group consisting of H and

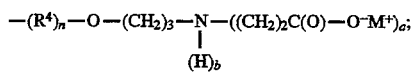

$R^4$ is lower alkyl selected from the group consisting of $-CH_2-$ and $-CH(CH_3)-$;

M is hydrogen or any positively charged salt forming radical;

n is an integer from 1 to 3.

2. A compound of claim 1 wherein $R^3$ is H.

3. A compound of claim 1 wherein $R^3$ is:

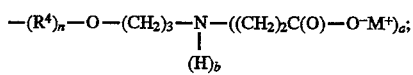

4. A compound of claim 1 wherein $R^4$ is $-CH_2-$.
5. A compound of claim 1 wherein $R^4$ is $-CH(CH_3)-$.
6. A compound of claim 2 wherein $R^4$ is $-CH_2-$.
7. A compound of claim 2 wherein $R^4$ is $-CH(CH_3)-$.
8. A compound of claim 3 wherein $R^4$ is $-CH_2-$.
9. A compound of claim 3 wherein $R^4$ is $-CH(CH_3)-$.
10. A compound of claim 1 wherein $R^1$ is alkyl having 5 carbon atoms.
11. A compound of claim 1 wherein $R^1$ is alkyl having 7 carbon atoms.
12. A compound of claim 1 wherein $R^1$ is alkyl having 9 carbon atoms.
13. A compound of claim 1 wherein $R^1$ is alkyl having 11 carbon atoms.
14. A compound of claim 1 wherein $R^1$ is alkyl having 13 carbon atoms.
15. A compound of claim 1 wherein $R^1$ is alkyl having 15 carbon atoms.
16. A compound of claim 1 wherein $R^1$ is alkyl having 17 carbon atoms.
17. A compound of claim 1 wherein $R^1$ is alkyl having 19 carbon atoms.

* * * * *